United States Patent [19]

Re et al.

[11] 4,008,363

[45] Feb. 15, 1977

[54] PROCESS FOR THE PREPARATION OF ADENINE DERIVATIVES MADE FUNCTIONAL AND PRODUCTS OBTAINED THEREFROM

[75] Inventors: Luciano Re, Rome; Piergiorgio Zappelli, Monterotondo, both of Italy

[73] Assignee: Snam Progetti S.p.A., Milan, Italy

[22] Filed: Apr. 29, 1975

[21] Appl. No.: 572,653

[30] Foreign Application Priority Data

Apr. 30, 1974 Italy ............................... 22105/74

[52] U.S. Cl. .................................. 536/28; 195/52; 536/29
[51] Int. Cl.² ....................................... C07H 19/20
[58] Field of Search ............... 260/211.5 R; 536/28

[56] References Cited

UNITED STATES PATENTS 3,287,352 11/1966 Wiley ........................... 260/211.5 R
3,475,408 10/1969 Kuhn et al. .................. 260/211.5 R

*Primary Examiner*—Johnnie R. Brown
*Attorney, Agent, or Firm*—Ralph M. Watson

[57] ABSTRACT

Nicotinamide 6-(2-hydroxy-3-carboxy-propylamino) purine dinucleotide is prepared by reacting nicotinamide-adenine-dinucleotide with 3,4 epoxybutanoic acid in the presence of perchloric acid to prepare an intermediate wherein the adenine nucleus is alkylated in the $N_1$ position. That intermediate is subjected to chemical reduction of the nicotinamide ring, followed by rearrangement to yield the end product wherein the amino group in position 6 of the adenine ring is alkylated.

2 Claims, 1 Drawing Figure

TABLE I
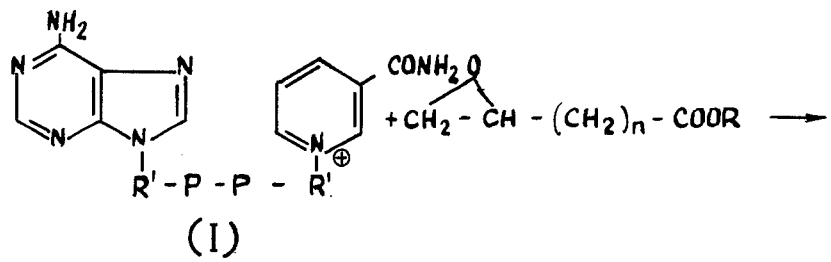
(I)
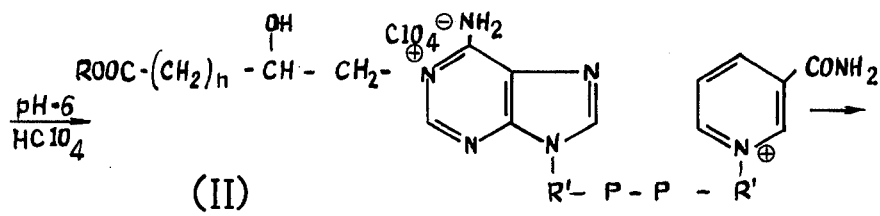
(II)
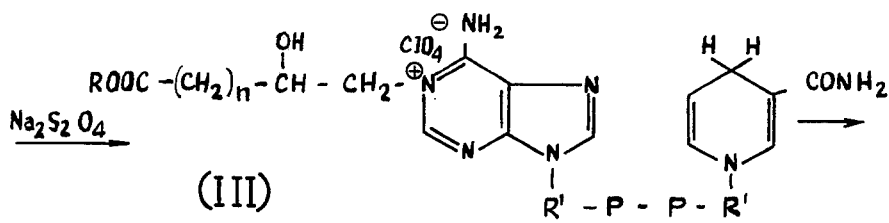
(III)
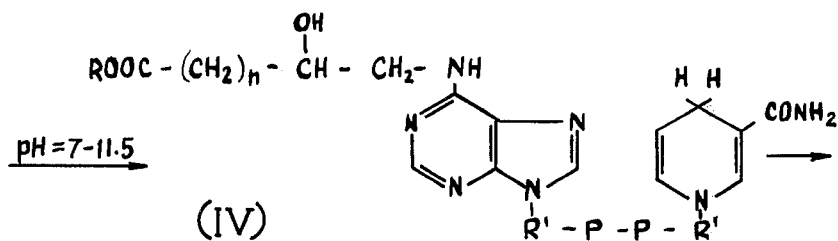
(IV)
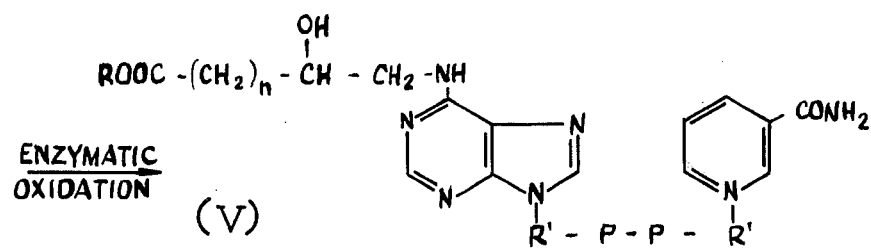
(V)
-R' = RIBOSE ; P = PHOSPHOROUS ; n = 1, 2, 3, 4 ; R = H, ALKYL, etc.

PROCESS FOR THE PREPARATION OF ADENINE DERIVATIVES MADE FUNCTIONAL AND PRODUCTS OBTAINED THEREFROM

The present invention relates to a process for the preparation of Adenine derivatives made functional and to the products obtained therefrom.

More specifically the present invention concerns a process for converting to a functional the amino group in position 6 in the Adenine nucleus, as shown in the following formula:

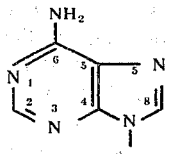

starting from products containing such nucleus such as, e.g. nicotinamide-adenine-dinucleotide, nicotinamide-adenine-dinucleotide phosphate, adenosine-monophosphate, cyclic adenosine-monophosphate, adenosine-diphosphate, adenosine-triphosphate, adenosine, adenine.

Most of these products are of great importance in biochemistry and the possibility of converting the amine to a functional group widens the field of application.

For instance in the case of nicotinamide-adenine-dinucleotide (NAD), and the same applies to other cases, its derivatives made functional may be used, after being linked with a co-valence to water soluble or water insoluble molecules, in affinity chromatography or as non-diffusing co-enzymes.

Thus, in the case of attack on water soluble macro-molecules, they may be used as macro-molecular, water-soluble, non-diffusing co-enzymes. Such co-enzymes enable the widening of the field of application of known enzyme systems, where the enzyme is physically embodied in insoluble structures, such as fibres, polyacrylamide gel, micro-capsules, etc., impervious to macro-molecules.

Thus, by physically embodying the enzyme or the polyenzyme system with the macro-molecular water soluble co-enzyme, both enzyme and co-enzyme remain in close contact and one avoids the dispersion of the latter outside the embodying structure, whilst so far this was impossible because of the low molecular weight of the co-enzyme.

In case of attack on water insoluble macro-molecules, they can be used for affinity chromatography or for enzyme reactions in the heterogeneous phase, with the possibility of recovering the enzyme.

According to the present invention the new function-carrying derivatives are prepared by reacting the starting compound containing the adenine nucleus with epoxides of acids or carboxylic esters

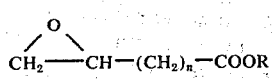

where R may be hydrogen, alkyl, cycloalkyl, aryl, arylalkyl and n a non-fractional number between 1 and 4.

The reaction is carried out at temperatures varying from 0° to 50° C, preferably at room temperature and in the presence of a solvent generally chosen from water soluble organic solvents or mixtures thereof, keeping the pH at about 6 by adding perchloric acid.

The reaction causes an alkylation of the nitrogen in position 1 of the adenine nucleus as illustrated in the formula

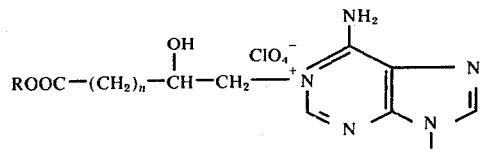

The product thus obtained is converted to the function carrying derivative with the following formula

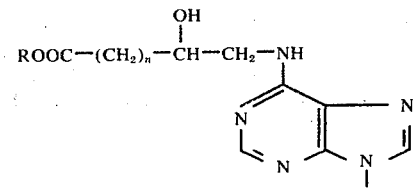

by re-arrangement effected at a pH between 7 and 11.5 and temperature between +5° and +80° C, preferably at pH 11.2 and at 75° C.

In the above formulae n and R have their well-known meaning. In case of the simultaneous presence of one nicotinamide nucleus it is preferable to effect a reduction of the same, before rearranging.

As we said, the process is absolutely general.

We shall refer, however, in the course of this specification, to the process of making the NAD functional and, for demonstration purposes, to the individual steps necessary to carry out said process. It will be apparent, however reading what follows, that any expert in the art will be able to obtain function-carrying adenine derivatives starting from any adenine basis, by simply adjusting the operating conditions to the starting compound, without coming outside the scope of the present invention.

More specifically the preparation fo function carrying NAD derivatives is carried out by reacting NAD with the epoxy-acid or ester, in water or water solution with ordinary organic water-soluble solvents and keeping the pH around 6 with perchloric acid: in this way we obtain the product of the nitrogen alkylation in position 1 of the adenine nucleus. The product obtained is then subjected to a chemical reduction of the nicotinamide ring, followed by rearrangement, to yield the product of the alkylation of the amino group in position 6 of the adenine group.

Finally by enzyme re-oxidation of the nicotinamide ring with a de-hydrogenase we obtain the function carrying derivative of NAD. It must be noticed that, once the position 1 of the adenine nucleus of NAD is alkylated, all the successive reactions may be carried out in the same reaction vessel without isolating the intermediate products.

All the operating conditions and details will be made evident by the examination of the examples which, we repeat, are reported for the sole purpose of better clarifying the invention without limiting the scope.

EXAMPLE 1

3,4 epoxybutanoic acid

To 9.46 g (110 m.moles) of 3-butenoic acid, dissolved in 30 ml of $CH_2Cl_2$ cooled at 0° C, 110 m.moles of peracetic acid in 80% solution (prepared according to H. Krimm, U.S. Pat. No. 2,813,896 (1957)) were added.

The reaction mixture was taken to room temperature in a water bath.

After four days of stirring at room temperature, further 25 m.moles of peracetic acid were added. The gas chromatography check 24 hours after the second addition of the peracid showed the disappearance of the 3-butenoic acid. The reaction mixture was then concentrated at 50° C and 20 mmHg and the residue underwent 5 successive washes with cyclohexane, and 3 with toluene under the previous conditions of vacuum and temperature, in order to completely remove the acetic acid. The yield is g 10.27 of 3,4-epoxybutanoic acid with gas chromatography purity of 90% after esterification with diazomethane. The NMR test and Gas Mass carried out on the methyl ester confirm the structure of the structure of the product obtained.

EXAMPLE 2

3,4 methyl-epoxybutanoate

To 25.5 g (225 m.mole) of 3-methyl butenoate in 100 ml of $Et_2O$ cooled at 0° C, 406 m.moles of peracetic acid in 80% solution, were slowly added stirring the mixture.

The reaction was carried out at room temperature for 10 days. Then 100 ml of $CH_2Cl_2$ were added and the organic mixture was washed with small quantities of saturated $NaHCO_3$ solution till neutral.

The organic phase was dried on anhydrous $Na_2SO_4$ and concentrated at 45° C at atmospheric pressure.

The residual was distilled on Spinning Band columns under 0.02 mmHg vacuum, collecting the product which distills at 30° C.

One obtained 11.38 g of 3,4 methyl-epoxybutanoate which was found pure under the gas chromatography and NMR test and identical to that prepared by esterification of 3.4 epoxybutanoic acid with diazomethane.

EXAMPLE 3

Preparation of nicotinamide 6-(2-hydroxy-3 carboxypropyl amino) purine dinucleotide V($n=1$, R = H). The 1 g (1.51 m.moles) of NAD dissolved in 6 ml bi-distilled water were added 42.1 m.moles of 3,4 epoxybutanoic acid brought to pH 6 at 0° C with NaOH 6 N. The pH of the mixture was further adjusted to 6 and the reaction flask protected from the light and provided with magnetic stirrer is connected to a pH -meter and automatic burette loaded with 1 N perchloric acid in order to keep the pH of the reaction mixture at 6 during all the course of the reaction. After 8 days stirring at room temperature the reaction was stopped (TLC check) and after acidifying to pH 4 with 1 N perchloric acid the product is precipitated by adding ten volumes of acetone and settling the suspension over night at about −20° C, collected after centrifying and finally dried on a rotating evaporator.

The ultraviolet spectrum in $Na_2CO_3O$, 1 N of such product (II, $n=1$, R=H) shows an absorption with a peak at 259 m $\mu$ and two slopes at 267 and $\eta$ 290 m $\mu$ characteristic of an adenine nucleus alkylated in $N_1$. The product thus isolated is redissolved in 60 ml of $NaHCO_3$ 1%, added with 400 mg of $Na_2S_2O_4$ and heated in a boiling water bath for 5 minutes to give III ($n=1$, R=H).

After a rapid cooling air is bubbled through the solution for 15 minutes to destroy the excess of $Na_2S_2O_4$.

The ultraviolet spectrum of the solution obtained shows, on top of the peak at 259 and the two slopes at 267 at $\eta$ 290 m $\mu$ the appearance of a new peak of absorption at 340 m $\mu$ which shows the actual reduction of the nicotinamide ring.

The solution is brought to pH 11.2 with NaOH 1 N and heated at 75° C for one hour, then cooled at room temperature to give IV($n = 1$, R=H).

The ultraviolet spectrum of the solution obtained shows, not only the presence of a peak at 340 m $\mu$ but also the disappearance of the peak at 259 m $\mu$ and the slope at $\eta$ 290 m $\mu$ with the formation of a new peak at 267 m $\mu$ typical of the adenines alkylated with the amino group in position 6.

To the solution is added 3 ml of buffer solution TRIS 3M, brought to a pH 7.5 with 6 N HCl and there were finally added 0.5 ml acetaldeyde and 100 of a alcoholdehydrogenase solution from yeast in an ammonium sulfate 4.8 N (containing 29.4 mg enzyme per ml).

The ultraviolet spectrum of the solution obtained showed as well as the presence of a peak at 267 m $\mu$, the disappearance of the absorption peak at 340 m $\mu$, confirming the completed re-oxidation of the nicotinamide ring.

After acidifying to pH 3 with 6 N HCl, precipitation with 10 volumes of acetone and settling over night at about −20° C, the oily precipitate was collected and diluted with 100 ml of bi-distilled water, adjusted to pH 8 with 1 N NaOH and applied to a chromatography column containing 40 ml of anionic resin DOWEX 21 K in the $HCOO^-$ form.

It was diluted with a further 100 ml of bi-distilled water, then with 0.075 M HCOOH until the solution was shown to contain no more products absorbing UV around 260 m $\mu$.

The successive dilution with HCOOH $0.2^M$ (1.51) made it possible to collect the NAD derivative V ($n=1$, R=H).

The concentration by lypophilization at about 1/10 of the volume, the precipitation with 10 volumes of acetone, settling overnight at about −20° C and centrifuging made it possible to collect 190 mg of NAD derivative V ($n=1$, R=H) in a pure state.

The NMR test, IR and NaPH titrations confirm the structures of the product obtained (see table 1).

EXAMPLE 4

Preparation of nicotinamide 6(2-hydroxy-3 carbomethoxypropylamino) purine dinucleotide (V, $n=1$, R=$CH_3$).

1 g of NAD dissolved in 5 ml bi-distilled water was brought to pH 6 with 1 N NaOH and added with 5.25 g of 3,4-methyl epoxybutanoate.

The reaction flask protected from the light and provided with magnetic stirring was connected to a pH-meter and automatic burette loaded with 1 N $NClO_4$ to keep the pH of the mixture at 6 during all the course of the reaction.

After 4 days of stirring at room temperature the reaction was completed (TLC control) and after acidifying the solution to pH 4 with $HClO_4$ 1 N, precipitation with 10 volumes of acetone and overnight settling at −20° C the product II ($n=1$, R—CH) was collected and the residual acetone was removed with a rotating evaporator. UV according to structure.

The precipitate was dissolved in 60 ml of $NaHCO_3$ 1% added with 400 mg of $Na_2S_2O_4$, heated in boiling water bath for 5 minutes, quickly cooled and air blown for 15 minutes to give III ($n=1$, $R=CH_3$). UV according to structure. The solution was brought to pH 11.2 with 1 N NaOH, heated at 75° C for 1 hour, then cooled at room temperature to give IV ($n=1$, $R=CH_3$). UV according to structure.

The solution was then added with 3 ml of TRIS 3M buffer solution brought to 7.5 pH with HCl 6 N and finally added with 0.5 ml acetaldehyde and 100 $\mu$ 1 of a suspension of alcohol dehydrogenase from yeast in 4.8 ammonium sulfate solution (containing 29.4 mg of enzyme per ml).

The mixture was settled at room temperature in the darkness for 40 minutes, to give V ($n=1$, R=CH) UV according to structure.

The solution obtained was then acidified to pH3 with 6 N HCl, added with 10 volumes of acetone and the oily precipitate obtained after settling overnight at about −20° C was dissolved in 100 ml of bi-distilled water, brought to pH 8 with NaOH 1 N and applied to a chromatography column containing 40 ml of DOVEX 21 K resin in the $HCOO^-$ form.

It was diluted beforehand with a further 100 ml of bi-distilled water, then with HCOOH 0.075 M until no longer were diluted products absorbing UV around 260 m.

The successive elution with HCOOH 0.2 M allowed the collection of NAD derivative V($n=1$, $R=CH_3$) which was isolated in the pure state after concentration by lyophilization, precipitation with 10 volumes of acetone, settling overnight at about −20° C and centrifying.

The NMR and IR tests confirm the structure of the product obtained.

EXAMPLE 5

Preparation of nicotinamide 6-(2 hydroxy-3-carboxy-propylamino) purine di-nucleotide V($n=1$, R=H) from Dihydronicotinamide 6-(2-hydroxy-3-carbomethoxypropylamino) purine dinucleotide IV ($n=1$, $R=CH_3$).

1 g of Dihydronicotinamide 6-(2-hydroxy-3-carbomethoxypropylamico) purine dinucleotide IV ($n=1$, $R=CH_3$) was added with 15 ml of bi-distilled water, of 15 ml of 0.5 N NaOH in alcohol and heated at 75° C for 30 minutes. It was immediately cooled and the enzyme oxidation and the elaboration described in example N. 3 were carried out. The product this obtained is identical (TLC, NMR, IR, UV) to the product obtained in example 3.

We claim:
1. Nicotinamide 6-(2-hydroxy-3-carboxy-propylamino) purine dinucleotide.
2. Nicotinamide 6-(2-hydroxy-3-carbomethoxy-propylamino) purine dinucleotide.

* * * * *

UNITED STATES PATENT AND TRADEMARK OFFICE
CERTIFICATE OF CORRECTION

PATENT NO. : 4,008,363
DATED : February 15, 1977
INVENTOR(S) : Luciano Re and Piergiorgio Zappelli It is certified that error appears in the above-identified patent and that said Letters Patent are hereby corrected as shown below:

Column 1, line 10, After "functional" insert --group--.

line 30, After "amine" insert --group--.

Column 2, line 49, Correct spelling of "of".

Column 3, line 30, Before "m.moles", Correct "225"

to read --255--.

Column 4, line 63, Correct "$NClO_4$" to read --$HClO_4$--.

Column 5, line 6, After 1 % insert a comma --,--.

Signed and Sealed this

Twenty-first Day of June 1977

[SEAL]

Attest:

RUTH C. MASON
Attesting Officer

C. MARSHALL DANN
Commissioner of Patents and Trademarks